United States Patent [19]

Becker et al.

[11] 4,297,501

[45] Oct. 27, 1981

[54] PROCESS FOR THE PREPARATION OF URETHANES

[75] Inventors: Robert Becker; Johann Grolig, both of Leverkusen; Christian Rasp, Cologne, all of Fed. Rep. of Germany

[73] Assignee: Bayer Aktiengesellschaft, Leverkusen, Fed. Rep. of Germany

[21] Appl. No.: 125,394

[22] Filed: Feb. 27, 1980

[30] Foreign Application Priority Data

Mar. 2, 1979 [DE] Fed. Rep. of Germany ....... 2908251

[51] Int. Cl.$^3$ ............................................ C07C 125/065
[52] U.S. Cl. ........................................ 560/24; 560/25; 560/26; 560/27; 560/28; 560/30; 560/115; 560/133; 560/134; 560/135; 560/157; 560/158; 560/161; 560/162; 560/163; 560/164; 560/165; 560/166
[58] Field of Search .................... 560/24, 25, 26, 27, 560/28, 30, 115, 133, 134, 135, 157, 158, 162, 164, 163, 161, 165, 166

[56] References Cited

U.S. PATENT DOCUMENTS

| | | | |
|---|---|---|---|
| 3,531,512 | 9/1970 | Hardy et al. | 560/25 |
| 4,178,455 | 12/1979 | Hirai et al. | 560/25 |

FOREIGN PATENT DOCUMENTS 815 2/1979 European Pat. Off. .
1472243 5/1977 United Kingdom .

OTHER PUBLICATIONS

Kondo et al., Chemisry Letters, Chemical Society of Japan, pp. 373-374, 1972.

*Primary Examiner*—G. T. Breitenstein
*Attorney, Agent, or Firm*—Gene Harsh; Joseph C. Gil; Lyndanne M. Whalen

[57] ABSTRACT

A process for producing urethanes by reacting primary amines, carbon monoxide and organic hydroxyl compounds in the presence of molecular oxygen and/or organic nitro compounds as oxidizing agents and a catalyst system comprising a noble metal and/or a compound of a noble metal of the 8th subgroup of the Periodic System of Elements and a compound capable of undergoing Redox reactions under reaction conditions of the 3rd to 5th main group and/or 1st to 8th subgroup of the Periodic System of Elements.

9 Claims, No Drawings

PROCESS FOR THE PREPARATION OF URETHANES

FIELD OF THE INVENTION

This invention relates to an improved process for the preparation of urethanes by the reaction of primary amines with carbon monoxide and organic compounds having at least one hydroxyl group.

BACKGROUND OF THE INVENTION

Organic isocyanates are generally prepared on a large commercial scale by reacting the corresponding amines with phosgene. Because of the toxicity of phosgene, many attempts have been made to find a suitable method of synthesizing organic isocyanates on a large commercial scale without the use of phosgene. One such method consists of reacting organic nitro compounds with carbon monoxide and organic hydroxyl compounds to form the corresponding urethanes, followed by decomposition of the urethanes into isocyanates and hydroxyl compounds. Modification of the urethane obtained as an intermediate product before decomposition is also possible. Thus, for example, phenyl urethane which is obtainable from nitro benzene, carbon monoxide and ethanol could first be reacted with formaldehyde to form the bis-urethane of 4,4'-diisocyanatodiphenyl methane which could then be converted into 4,4'-diisocyanatodiphenyl methane by elimination of the ethanol.

The decomposition of urethanes into the corresponding isocyanates and hydroxyl compounds has been described, for example, in German Offenlegungsschrift No. 2,421,503 and the prior publications cited therein.

The reactions described in the patent literature for the preparation of urethanes include the reaction of nitro compounds with carbon monoxide and alcohols in the presence of selenium or selenium compounds as described in German Offenlegungsschriften Nos. 2,343,826; 2,614,101 and 2,623,694 or of noble metals, in particular palladium, in the presence of Lewis acids as described in German Offenlegungsschriften Nos. 1,568,044 and 2,603,574. For the preparation of a mono nitro compound this reaction proceeds in accordance with the following stoichiometric equation:

$$R-NO_2 + 3CO + R'OH \rightarrow RNHCO_2R' + 2CO_2.$$

The general reaction equation is as follows:

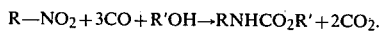

This means that for every mol of urethane group produced, 3 mol of carbon monoxide are used up and 2 mol of carbon dioxide are formed. Only one-third of the carbon monoxide put into the process is thus used for the formation of the urethane group while two-thirds are converted into the industrially valueless inert carbon dioxide. Because of the large quantity of heat produced in the exothermic formation of carbon dioxide, expensive apparatus for removal of this heat is required in the known industrial process of synthesizing urethane based on the use of nitro compounds, carbon monoxide and alcohol.

Chemistry Letters (Chemical Society of Japan), 1972, pages 373–374, describes reacting primary amines with stoichiometric quantities of selenium, a tertiary amine, carbon monoxide and alcohol to produce a complex salt from which the corresponding urethane is obtained by reaction with molecular oxygen, the selenium and tertiary amine both being recovered. This can be shown as follows:

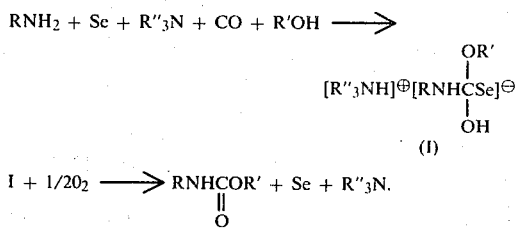

The overall reaction results in the formation of urethane in accordance with the following equation:

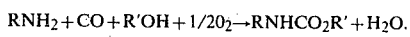

This overall reaction requires only 1 mol of carbon monoxide for each urethane group produced. The exothermic heat of reaction is, therefore, less since only 1 mol of water is formed instead of the 2 mol of carbon dioxide produced when nitro compounds are used. This oxycarbonylation "catalyst" with stoichiometric quantities of selenium is not, however, suitable for the synthesis of urethane on a commercial scale. This is because the method requires the use of unacceptably large quantities of selenium which is toxic, expensive and difficult to recover quantitatively from the reaction mixture. Moreover, the oxycarbonylation using selenium must be carried out in two stages, which adds to the difficulty of using this process on a large scale. Additionally, the yields obtained from this method are unsatisfactorily low.

DESCRIPTION OF THE INVENTION

It has now been found that an oxycarbonylation of primary amines to urethanes can be carried out in industrially acceptable yields without the use of carbon monoxide, with more efficient removal of heat and without the disadvantages entailed in the use of selenium, by reacting primary amines with carbon monoxide and organic compounds having at least one hydroxyl group in the presence of molecular oxygen and/or organic nitro compounds as oxidizing agents and in the presence of certain catalysts.

The present invention relates to a process for the preparation of urethanes comprising reacting primary amines with carbon monoxide and organic compounds having at least one hydroxyl group in the presence of (a) molecular oxygen and/or organic nitro compounds as oxidizing agent, (b) a noble metal and/or a noble metal compound of the 8th subgroup of the Periodic System of Elements, and (c) a compound of an element of the 3rd to 5th main group and/or the 1st to 8th subgroup of the Periodic System of Elements, said compound being capable of Redox reactions under the reaction conditions.

The primary amines used as starting materials for the instant process may be any primary amines having at least one aliphatically, cycloaliphatically and/or aromatically bound amino group. They generally have a molecular weight in the range of from 31 to 400, preferably 93 to 279.

The following are specific examples of suitable aromatic primary amines: aniline; 1,2-diaminobenzene; 1,3-diaminobenzene; 1,4-diaminobenzene; o-chloroaniline; m-chloraniline tolylidine; xylidines; 2,3-diamino-toluene; 2,4-diamino-toluene; 2,6-diamino-toluene; 3,4-diaminotoluene; 3,5-diamino-toluene; diamino-xylenes; 1-amino-naphthalene; 2-amino-nephthalene; diamino-naphthalene; amino-anthracenes; 4,4'-diamino-diphenyl methane; 2,2'-diamino-diphenyl methane and tris-(4-amino phenyl)-methane. The following are specific examples of cycloaliphatic primary amines: amino cyclobutane; amino cyclopentane; cyclohexylamine; 1,2-diamino cyclohexane; 1,3-diamino cyclohexane; 1,4-diamino cyclohexane; bis-(amino cyclohexyl)-methanes; tri-(amino cyclohexyl)-methanes. The following are specific examples of aliphatic primary amines: methylamine; ethylamine; 1-propylamine; 2-propylamine; 1-butylamine; 2-butylamine; isobutylamine; tertiary butylamine; 1-pentylamine; 1-hexylamine; 1-heptylamine; 1-octylamine; 1-decylamine; 1-dodecylamine; ethylene diamine; 1,2-diamino propane; 1,3-diamino propane; diamino butanes; diamino pentanes; diamino hexanes; diamino octanes; diamino decanes; benzylamine; bis-(aminomethyl)-cyclohexanes; bis-(aminomethyl)-benzene; -aminocarboxylic acid esters and -amino carboxylic acid nitriles.

Aromatic primary amines are particularly preferred. Specifically preferred are aniline; 1,3-diamino benzene; 2,4-diamino toluene; 2,6-diamino toluene and 1,5-diamino naphthalene.

The starting materials used for the instant process also include any organic compounds having hydroxyl groups. Examples of these include monohydric or polyhydric alcohols or monohydric or polyhydric phenols. Suitable alcohols include, for example, those having a molecular weight within the range of 32 to 300, preferably from 32 to 102. These may include any linear or branched chain monohydric or polyhydric alkanols or alkenols or any monohydric or polyhydric cycloalkanols, cycloalkenols or aralkyl alcohols. The alcohols may also have any inert substituent. Suitable substituents include, for example, halogen atoms, sulphoxide groups, sulphone groups, carbonyl groups and carboxylic acid ester groups. Alcohols having ether bridges are also suitable in principle. The following are specific examples of suitable alcohols: methanol, ethanol, n-propanol, isopropanol, n-butanol, n-pentanol, n-hexanol, cyclohexanol, benzyl alcohol, chloro-ethanol, ethylene glycol, diethylene glycol, propylene glycol, dipropylene glycol, glycerol, hexanetriol and trimethylol propane. Monohydric aliphatic alcohols having 1 to 6 carbon atoms are preferred.

Suitable phenols include in particular those having a molecular weight of from 94 to 300. Examples of these include phenol, the isomeric chloro phenols, cresols, ethyl phenols, propyl phenols, butyl phenols and higher alkyl phenols, pyrocatechol, 4,4'-dihydroxydiphenyl methane, bisphenol-A, anthranol, phenanthrol, pyrogallol and phloroglucinol. The alcohols are generally preferred over the phenols. Ethanol is the most preferred hydroxyl compound to be used in the process according to the invention.

When carrying out the instant process, the organic hydroxyl compounds are generally used in quantities providing from 1 to 100, preferably 1 to 20 mols of hydroxyl groups for each mol of primary amino groups present in the reaction mixture and for each mol of nitro groups, if present. Since the hydroxyl compounds used are generally liquid under the reaction conditions, any excess used serves as reaction medium (solvent) for the instant process.

The other reactant used in the instant process is carbon monoxide. This is generally used in a quantity corresponding to 1 to 30 mols of carbon monoxide per mol of urethane to be produced. This means that from 1 to 30 mols of carbon monoxide are put into the process for each mol of primary amino groups present in the reaction mixture and for each mol of the nitro groups, if present.

The instant reaction is carried out in the presence of an oxidizing agent and catalysts.

The oxidizing agent used may be molecular oxygen in the pure form or in the form of a mixture with an inert gas such as nitrogen or carbon monoxide, in particular in the form of air. In the presence of molecular oxygen, oxycarbonylation proceeds in accordance with the following general reaction equation:

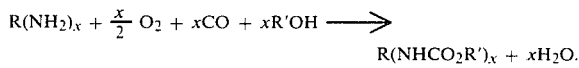

$$R(NH_2)_x + \frac{x}{2} O_2 + xCO + xR'OH \longrightarrow R(NHCO_2R')_x + xH_2O.$$

This means that only one mol of carbon monoxide is required for each urethane group formed.

Molecular oxygen serving as oxidizing agent may be used in less than the equivalent amount. An inert gas such as nitrogen or carbon dioxide is preferably added in such quantities that the reaction can proceed outside the range of explosion of oxygen-carbon monoxide or oxygen alcohol mixtures. If no inert gas is added, the quantity of oxygen added should be calculated to avoid the formation of explosive mixtures with the carbon monoxide and alcohol components. Molecular oxygen is preferably used in the form of air or a mixture of air and nitrogen. When molecular oxygen is used as the sole oxidizing agent, its quantity is preferably calculated so that at least half a mol of oxygen is available for each mol of primary amino groups present in the above reaction equation. Excess quantities of oxygen may, of course, also be used.

Organic nitro compounds are the preferred oxidizing agents. The nitro compound used may be completely different in structure from the primary amine so that although urethanes are obtained both from the primary amine and from the nitro compound, they are different from each other in structure. Oxycarbonylation may proceed in this case according to the following reaction equation:

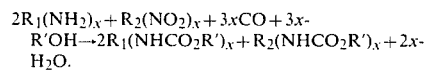

$$2R_1(NH_2)_x + R_2(NO_2)_x + 3xCO + 3xR'OH \rightarrow 2R_1(NHCO_2R')_x + R_2(NHCO_2R')_x + 2xH_2O.$$

In order to obtain the best possible yield, the quantities of primary amine and nitro compound used when organic nitro compounds are the sole oxidizing agent are preferably calculated to provide two amino groups for each nitro group in the reaction mixture. If the nitro compounds are present in less than the equivalent quantity, conversion of amine is incomplete. If the nitro compounds are present in stoichiometric excess, they are converted into urethane groups with the formation of carbon dioxide in accordance with the following reaction equation:

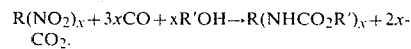

$$R(NO_2)_x + 3xCO + xR'OH \rightarrow R(NHCO_2R')_x + 2xCO_2.$$

The advantage of full utilization of the carbon monoxide is thus partly lost.

Strict observation of these proportions is, of course, not necessary. In particular, a smaller quantity of nitro compound may be used if molecular oxygen is used at the same time. In general, the nitro compounds should be added in such quantities that the equivalent ratio of the amino groups of the primary amines to the nitro groups is in the range of 1.1:1 to 4:1, in particular from 1.5:1 to 2.5:1 and most preferably from 1.8:1 to 2.2:1.

One particularly advantageous embodiment of the instant process consists of using nitro compounds which correspond to the primary amine in their structure so that 3 mols of urethane all having the same structure are obtained from 2 mols of primary amine and 1 mol of nitro compound as illustrated by the following reaction equation:

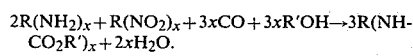

$$2R(NH_2)_x + R(NO_2)_x + 3xCO + 3xR'OH \rightarrow 3R(NH\text{-}CO_2R')_x + 2xH_2O.$$

Suitable nitro compounds for the instant process include any organic compounds having at least 1 aliphatically, cycloaliphatically and/or aromatically bound nitro group, and generally having a molecular weight in the range of from 61 to 400, preferably from 123 to 262.

The following are examples of suitable aromatic nitro compounds: nitrobenzene, o-dinitrobenzene, m-dinitrobenzene, p-dinitrobenzene, o-chloro-nitrobenzene, m-chloro-nitrobenzene, o-chloro-nitrobenzene. Also suitable are o-nitrotoluene, m-nitrotoluene, p-nitrotoluene, 2,3-dinitrotoluene, 2,4-dinitrotoluene, 2,5-dinitrotoluene, 2,6-dinitrotoluene and 3,4-dinitrotoluene. Examples of suitable xylenes are 3-nitro-o-xylene, 4-nitro-o-xylene, 2-nitro-m-xylene, 4-nitro-m-xylene, 5-nitro-m-xylene, nitro-p-xylene, 3,4-dinitro-o-xylene, 3,5-dinitro-o-xylene, 3,6-dinitro-o-xylene, 4,5-dinitro-o-xylene, 2,4-dinitro-m-xylene, 2,5-dinitro-m-xylene, 4,5-dinitro-m-xylene, 4,6-dinitro-m-xylene, 2,3-dinitro-p-xylene and 2,6-dinitro-p-xylene. Suitable naphthalenes include, for example, 1-nitro naphthalene, 2-nitro naphthalene and dinitro naphthalene. Still other suitable examples are nitro anthracenes, nitrodiphenyls, bis-(nitrophenyl)-methanes, bis-(nitrophenyl)-thioethers, bis-(nitrophenyl)-sulphones, nitrodiphenyl alkanes and nitrophenothiazines.

The following are examples of suitable cycloaliphatic nitro compounds: nitro cyclobutane, nitro cyclopentane, nitro cyclohexane, 1,2-dinitro cyclohexane, 1,3-dinitro cyclohexane, 1,4-dinitro cyclohexane and bis-(nitrocyclohexyl)-methanes.

Suitable nitro alkanes are, for example, nitro methane, nitro ethane, 1-nitro propane, 2-nitro propane, nitro butanes, nitro pentanes, nitro hexanes, nitro decanes, nitrocetanes, 1,2-dinitro ethane, 1,2-dinitro propane, 1,3-dinitro propane, dinitro butanes, dinitro pentanes, dinitro hexanes, dinitro decanes, phenyl nitro methane, bis-(nitro methyl)-cyclohexanes, bis-(nitromethyl)-benzenes and ω-nitro carboxylic acid nitriles.

The aromatic nitro compounds are the preferred nitro compounds for the instant process. The following nitro compounds are particularly preferred: nitro benzene, 1,3-dinitro benzene, 2,4-dinitro toluene, 2,6-dinitro toluene and, for example, 1,5-dinitro naphthalene.

The catalyst systems used in the instant process contain: (b) noble metals of the 8th subgroup of the Periodic System as their main constituent and (c) a co-catalyst component.

The catalyst component (b) may consist of free noble metals of the 8th subgroup of the Periodic System or of compounds of these metals soluble in the reaction mixture. It is particularly advantageous to use these noble metals in the form of compounds which are soluble in the reaction mixture, for example, as chlorides, bromides, iodides, chloro complexes, bromo complexes, iodo complexes, acetates, acetyl acetonates and other soluble noble metal compounds. Palladium and rhodium are the preferred noble metals. Palladium is particularly preferred, especially in the form of soluble palladium chloride. The preferred concentrations, based on the quantity of reaction mixture including any solvents used, are generally in the range of 0.0001 to 0.1% by weight, in particular 0.001 to 0.01% by weight, calculated as the noble metal. At lower concentrations of noble metal, the reaction velocity is too low. Although higher concentrations of noble metal could be used, this is uneconomical because of the possible loss of noble metal, especially costly since it does not result in any increase in the yield of urethane.

The co-catalysts (c) may be any compounds of the elements of the 3rd to 5th main group and 1st to 8th subgroup of the Periodic System which are capable both as compounds and as elements, of undergoing Redox reactions under the reaction conditions, and are different from component (b). The compounds are preferably chlorides, oxychlorides, oxides and/or hydroxides of these elements, and if oxides or hydroxides are used, certain chlorides which have an activating action are preferably added.

The following are examples of suitable co-catalysts: copper(II)chloride; thallium(III)chloride; tin(II)chloride, tin(IV)chloride; arsenic(III)chloride; bismuth(III)chloride; vanadium(III)chloride; chromium(III)chloride, molybdenum(IV) chloride, tungsten(V)chloride; tungsten(VI)chloride; manganese(II)chloride; iron(II)chloride; iron(III)chloride; iron oxychloride; cobalt(II)chloride; copper(II)oxide; copper(II)hydroxide; thallium(I)hydroxide; tin(II)oxide; tin(II)hydroxide, vanadium pentoxide; molybdenum trioxide; tungsten trioxide; manganese dioxide; iron(II)oxide; iron(II)hydroxide; iron(III)hydroxide; iron(III)oxides such as, for example, α-Fe$_2$O$_3$ or γ-Fe$_2$O$_3$; hydrated iron(III) oxides such as, for example, α-FeO-OH, β-FeO-OH or γ-FeO-OH; and iron spinel Fe$_3$O$_4$.

The particularly preferred co-catalysts include iron(II)chloride; iron(III)chloride; iron oxychloride and the oxides and hydrated oxides of trivalent iron.

If the oxides or hydroxides exemplified above are used, which are often completely inert under the reaction conditions, it is necessary to add activating chlorides. These activating chloride compounds contain anionic chloride bound as chlorides and are capable of reacting with the exemplified oxides and hydroxides under the reaction conditions to convert them at least partly into the corresponding chlorides or oxychlorides. Suitable activating chlorides include, for example, the hydrochlorides of tertiary amines having a molecular weight in the range of 59 to 300, hydrochlorides of the primary amines used in the instant process, hydrogen chloride, iron(II)chloride and iron(II)chloride complexes. The following activating chlorides are particularly suitable: pyridine hydrochloride, aniline hydrochloride, the hydrochlorides of 2,4-diamino toluene and 4,4'-diamino diphenylmethane, hydrogen chloride, iron(II)chloride and iron(II)chloride complexes. Combinations of the last mentioned, particularly preferred, activating chlorides with the oxides and hydrated oxides of trivalent iron are particularly valuable co-catalysts (c).

The concentrations at which the co-catalysts including the activating chlorides are used in the instant process are from 0.1 to 20% by weight, preferably from 1 to 5% by weight, based on the reaction mixture including any solvents used. Where activating chlorides are required, the proportion in which they are used is generally from 0.05 to 10% by weight, preferably from 0.1 to 2.5% by weight, based on the reaction mixture including any solvents used.

The instant reaction may be carried out in the presence or absence of a solvent. The organic hydroxyl compound, preferably used in excess, generally serves as solvent. Inert solvents may also be used in quantities of up to 80% by weight of the total reaction mixture. Regardless of whether the solvent is a hydroxyl compound used in excess or an inert solvent, the quantity in which it is used must be calculated so that the heat of reaction of exothermic urethane formation can be removed without unacceptable rise in temperature. The instant process is, therefore, generally carried out using a concentration of amino compounds of from 5 to 50% by weight, preferably from 5 to 20% by weight. If organic nitro compounds are used as oxidizing agents, they are used at a concentration of 1 to 20% by weight, preferably 5 to 10% by weight, based on the whole reaction mixture including solvent.

The solvents used should be inert towards the reactants and the catalyst system. Suitable examples are aromatic, cycloaliphatic and aliphatic hydrocarbons which may be substituted with halogen. These include solvents such as benzene, toluene, xylene, chlorobenzene, dichlorobenzene, trichlorobenzene, chloronaphthalene, cyclohexane, methyl cyclohexane, chlorocyclohexane, methylene chloride, carbon tetrachloride, tetrachloride and trichloro-trifluoro-ethane.

The reaction temperature is generally in the range of 100° C. to 300° C., in particular from 130° C. to 250° C. and most preferably in the range of from 140° C. to 220° C. The pressure should be such that a liquid phase is always present, and is generally in the range of 5 to 500 bar, most preferably from 30 to 300 bar, at the reaction temperature. The reaction time required for quantitative conversion ranges from a few minutes to several hours, depending on the primary amine and hydroxyl compound used, and the organic nitro compound, if any.

The oxycarbonylation of the primary amines with hydroxyl compounds, carbon monoxide and oxidizing agent to urethanes may be carried out batchwise or continuously.

The batchwise reaction may be carried out in a high pressure autoclave with small quantities of homogeneously dissolved noble metal and a sufficient excess of catalyst, optionally in the presence of an activating chloride. Compounds which are insoluble in the reaction medium, such as for example, iron oxides or hydrated iron oxides may be added in the form of a fine powder. The activating additives may be added in the form of a homogeneous alcoholic solution. Any undissolved excess co-catalyst constituents can be distributed in the reaction mixture by vigorous stirring or by circulating the reaction mixture with pumps. The exothermic heat of reaction may be removed by means of internally installed cooling apparatus or, if the reaction mixture is circulated with pumps, it may also be removed through an external heat exchanger. Working up of the reaction product and return of the catalyst may be carried out by various methods, depending on the solubility of the resulting urethane in the reaction mixture. If the urethanes are readily soluble, for example, the major quantity of the co-catalyst mixture which is only sparingly soluble at low temperatures, together with the major quantity of absorbed palladium and organic amine salt, may be separated from the reaction product after completion of the reaction, for example, by filtration or centrifuging and returned for a fresh reaction of primary amines, hydroxyl compounds, carbon monoxide and oxidizing agent. The liquid reaction mixture can be separated into solvent, pure urethanes and any small quantities of by-products present by the usual methods, e.g. by fractional distillation, either continuously or batchwise. The distillation residue will contain small quantities of co-catalyst constituents dissolved in the reaction mixture and/or traces of noble metal and/or noble metal compounds which may be returned to the reaction.

If the urethanes obtained are only sparingly soluble in the solvent or excess hydroxyl compound, the reaction mixture may be worked up by a different method. For example, after release of pressure, the major quantity of catalyst may be filtered or centrifuged off under a pressure and at an elevated temperature at which the urethanes are still soluble but most of the catalyst system of noble metal/co-catalyst mixture precipitates, and the sparingly soluble by-products and the remaining catalyst may then be crystallized by lowering the temperature. The mother liquor, which in addition to solvent or excess organic hydroxyl compound used as solvent still contains small quantities of by-products, dissolved urethane and possibly dissolved co-catalyst constituents, may then either be returned directly to the process of oxycarbonylation of the primary amines with hydroxyl compounds, carbon monoxide and oxidizing agent or the low boiling by-products present in it may first be removed, for example by distillation. When the mother liquor is returned to the process, the quantities of primary amine, hydroxyl compound and, if indicated, nitrocompound used as oxidizing agent which have been used up in the previous reaction are replaced. Higher boiling by-products which are not removed by crystallization may be removed continuously as distillation residue from the return stream by distilling an aliquot portion of the mother liquor. The precipitated crude urethane may, for example, by recrystallized from a solvent which dissolves the urethane at elevated temperatures but not the by-products and catalyst residues. Examples of such solvents include isooctane, benzene, toluene, xylene, chlorobenzene and dichlorobenzene. The residues which are insoluble at the elevated temperature may be converted by oxidation into insoluble oxides such as iron oxides and an exhaust gas resulting from the organic impurities. This gas consists mainly of carbon dioxide, oxygen, nitrogen and possibly highly volatile organic impurities. Depending on its composition, this exhaust gas may either be directly discharged into the atmosphere or transferred to a catalytic after-burning process in which residues of impurities are removed by oxidation. The oxidic compound obtained from the residue, which may still contain small quantities of noble metal and/or noble metal compounds is returned to the oxycarbonylation process.

The reaction gas obtained from the oxycarbonylation which may contain unreacted carbon monoxide, low boiling organic constituents, small quantities of carbon dioxide and, when molecular oxygen is used as oxidizing agent, also small quantities of unreacted oxygen, as well as the additional inert gas introduced, such as for example, nitrogen, may for example be readjusted to the reaction pressure after removal of the low boiling organic by-products and, if present, carbon dioxide and then returned to the reaction while the portions of carbon monoxide and possibly molecular oxygen used up are replaced.

The continuous reaction may be carried out in a cascade of reaction vessels, a system of pipes, a plurality of reaction coils arranged one behind the other, in an adiabatic reaction tube or in several such tubes connected in series, or in a bubble column. The heat may be removed internally, for example, by means of internal cooling assemblies, or externally through a system of heat exchange pipes or adiabatically through the thermal capacity of the reaction mixture, followed by cooling in external cooling assemblies.

Subsequent working up may be carried out as described above, either continuously or discontinuously.

For their preferred use as intermediate products for the production of the corresponding isocyanates, the products obtained from the instant process need not be pure in many cases. In these cases, the crude products obtained after removal of the catalyst by filtration and, if indicated, removal of the solvent by distillation, are ready for further use.

The following examples are provided to illustrate the process without restricting the invention in any way to the conditions given in the examples.

EXAMPLES

Example 1

250 g (270 ml) of a mixture of the following composition are introduced into a 0.7 liter stainless steel autoclave:

$2 \times 10^{-3}$% by weight palladium chloride, 4% by weight iron oxychloride, 5% by weight aniline and 91% by weight ethanol. 100 bar of carbon monoxide and 25 bar of air are then forced in at room temperature. The reaction mixture is heated to 150° C. and left to react at this temperature for two hours. After cooling to room temperature, the pressure was released and the liquid phase and gaseous phase were analyzed using gas chromatography. The aniline conversion was calculated to be 77% and the following phenyl urethane selectivities were calculated:

90% based on aniline, 95% based on ethanol and 78% based on carbon monoxide. The selectivity of carbon monoxide both here and in the following examples was calculated on the stoichiometric basis of 1 mol of carbon monoxide for each urethane group.

Example 2

The same procedures as in Example 1 was employed but rhodium chloride was used instead of palladium chloride. 50% of the aniline was converted after a reaction time of two hours at 180° C. Phenyl urethane was obtained in a selectivity of 60% based on aniline and 90% based on ethanol.

Example 3

The procedure was substantially the same as in Example 1 but using, as co-catalyst, a mixture of 4% by weight of $\alpha$-Fe$_2$O$_3$ and 1% by weight of FeCl$_2$.4 H$_2$O. After a reaction time of one hour at 180° C., 60% of the aniline had been converted. The urethane selectivities were 75% based on aniline, 94% based on ethanol and 88% based on carbon monoxide.

Example 4

100 bar of carbon monoxide and 25 bar of air were forced into 250 g (270 ml) of the mixture of $2 \times 10^{-3}$% by weight of palladium chloride, 2.8% by weight of MnO$_2$, 1.9% by weight of HCl (anhydrous) and 5% by weight of aniline in ethanol in a 0.7 liter autoclave at 20° C. The reaction mixture was rapidly heated to 180° C. and left at this temperature for one hour. It was then cooled to 40° C. and, after release of pressure, it was again reacted with the same quantity of carbon monoxide and air at 180° C. for one hour. The aniline conversion was 78% and the phenyl urethane selectivities were:

71% based on aniline, 99% based on ethanol and 76% based on carbon monoxide.

Example 5

250 g of a mixture of $2 \times 10^{-3}$% by weight of palladium chloride, 4% by weight of iron oxychloride and 20% by weight of a mixture of aniline and nitrobenzene in ethanol containing aniline and nitrobenzene in a molar ratio of 2:1 were introduced into a 0.7 liter stainless steel autoclave and 120 bar of carbon monoxide were forced in at room temperature. The reaction mixture was rapidly heated to 160° C. and left at this temperature for two hours. After cooling and release of pressure, gas chromatographic analysis produced the following results:

85% of the aniline was converted and nitrobenzene was converted quantitatively. The phenyl urethane selectivities were:

96% based on aniline and nitrobenzene, 99.3% based on ethanol and 77% based on carbon monoxide.

Example 6

The procedure of Example 5 was repeated with the following alterations: methanol was used instead of ethanol and the reaction time was five hours. Aniline conversion was calculated to be 97% and nitrobenzene conversion, 92%. N-phenyl-urethane was obtained in a yield of 85% based on reacted aniline and nitrobenzene and 93% based on reacted carbon monoxide.

Examples 7 to 14

The following table shows the results of oxycarbonylation of aniline with nitrobenzene in ethanol using different co-catalysts.

| | |
|---|---|
| PdCl$_2$ | $2 \times 10^{-3}$% by weight |
| Concentration of aniline + nitro benzene in ethanol | 20% by weight |
| Molar ratio aniline:nitrobenzene | 2:1 |
| Temperature °C. | 180 |
| Pressure bar | 120 at 20° C. |
| Reaction time h | 1 |

Results

| Example Number | Co-catalyst (% by weight) | Conversions % Aniline | Conversions % Nitro-Benzene | Phenyl urethane selectivity % based on Aniline + Nitrobenzene | Phenyl urethane selectivity % based on Ethanol | Phenyl urethane selectivity % based on CO |
|---|---|---|---|---|---|---|
| 7 | CuCl$_2$ (3,3) + V$_2$O$_5$ (2) | 75 | 100 | 85 | 95 | 95 |
| 8 | FeCl$_2$ . 4 H$_2$O (2) | 80 | 100 | 95 | 98 | 90 |
| 9 | FeCl$_3$ (4) | 90 | 100 | 90 | 95 | 80 |
| 10 | FeCl$_3$ (2) | 85 | 93 | 100 | 98 | 90 |
| 11 | α-Fe$_2$O$_3$ (2) + FeCl$_2$ 4 H$_2$O (0.6) | 80 | 100 | 96 | 99 | 90 |
| 12 | α-Fe$_2$O$_3$ (2.8) + aniline . HCl (3.6) | 90 | 100 | 90 | 99 | 85 |
| 13 | VCl$_3$ (2) | 76 | 100 | 95 | 90 | 85 |
| 14 | V$_2$O$_5$ (2.8) + aniline . HCl (3.6) | 80 | 100 | 98 | — | 85 |

Example 15

120 bar of carbon monoxide were forced into 250 g of a mixture of $2\times10^{-3}$% by weight of palladium chloride, 3.7% by weight of iron oxychloride, 7.4% by weight of aniline and 3.0% by weight of 2,4-dinitrotoluene in ethanol in a 0.7 liter autoclave and the mixture was reacted at 180° C. for two hours. 90% of the aniline was converted. The polyurethane selectivity was calculated to be 93% based on aniline.

Example 16

120 bar of carbon monoxide were forced into 250 g of a mixture of $2\times10^{-3}$% by weight of palladium chloride, 2.7% by weight of α-Fe$_2$O$_3$, 0.8% by weight of FeCl$_2$.4 H$_2$O, 4.5% by weight of 2,4-diaminotoluene and 6.5% by weight of 2,4-dinitrotoluene in ethanol at room temperature in a 0.7 liter autoclave and the mixture was reacted at 180° C. for two hours. Both 2,4-diaminotoluene and 2,4-dinitrotoluene were converted quantitatively. The following selectivities were obtained, based on the sum of diamine plus dinitro compounds:

75% bis-urethane of 2,4-diisocyanatotoluene, 15% monourethane mixture and 7% nitroaminotoluenes.

Example 17

This example illustrates the catalytic activity of rhodium compounds in the oxycarbonylation of primary amines with nitro compounds. 250 g of a reaction mixture having the following composition were introduced into the reaction vessel:

$2.7\times10^{-3}$% by weight rhodium trichloride, 3.7% by weight iron oxychloride, 11.6% by weight aniline and 7.67% by weight nitrobenzene. 120 bar of carbon monoxide were forced into the reaction mixture in a 0.7 liter autoclave at room temperature and the mixture was then reacted for one hour at 180° C. 59% of the aniline and 60% of the nitrobenzene were converted. The phenyl urethane yield, based on the sum of reacted aniline+nitrobenzene, was calculated from gas chromatographic analysis to be 85 mol %.

What is claimed is:

1. A heat efficient process for the preparation of urethanes comprising reacting primary amines with carbon monoxide and organic compounds having at least one hydroxyl group in the presence of
   (a) molecular oxygen as oxidizing agent,
   (b) a noble metal and/or a compound of a noble metal of the 8th subgroup of the Periodic System of Elements, and
   (c) a compound of an element of the 3rd to 5th main group and/or 1st to 8th subgroup of the Periodic System of Elements, said compound being capable of undergoing Redox reactions under the reaction conditions.

2. A process as claimed in claim 1 wherein said primary amine is an aromatic amine containing one or two primary amino groups.

3. A process as claimed in claim 1 wherein said compound (b) consists of palladium, rhodium, palladium compounds and/or rhodium compounds.

4. A process as claimed in claim 1 wherein said organic hydroxyl compound is a monohydric primary aliphatic alcohol having 1 to 6 carbon atoms.

5. A process as claimed in claim 1 wherein said reaction is carried out at a temperature of from 100° to 300° C. and at a pressure of from 5 to 500 bar.

6. The process of claim 1 wherein component (a) further includes an organic nitro compound.

7. A heat efficient process for the preparation of urethane comprising reacting primary amines with carbon monoxide and organic compounds having at least one hydroxyl group in the presence of
   (a) molecular oxygen and/or organic nitro compounds as oxidizing agents, in an amount such that when an organic nitro compound is used as the oxidizing agent, the molar ratio of primary amine to nitro compound is at least 1.1 to 1,
   (b) a noble metal and or a compound of the noble metal of the 8th subgroup of the Periodic System of Elements, and
   (c) an oxychloride of elements of the 3rd to 5th main group or 1st to 8th subgroup of the Periodic System of Elements capable of undergoing Redox reaction under reaction conditions.

8. A process as claimed in claim 7 wherein said component (c) is iron oxychloride.

9. A heat efficient process for the preparation of urethanes comprising reacting primary amines with carbon monoxide and organic compounds having at least one hydroxyl group in the presence of
   (a) molecular oxygen and/or organic nitro compounds as oxidizing agent,
   (b) a noble metal and/or a compound of a noble metal of the 8th subgroup of the Periodic System of Elements, and
   (c) mixtures of (1) oxides and/or hydroxides of elements of the 3rd to 5th main group and 1st to 8th subgroup of the Periodic System of Elements capable of undergoing Redox reactions under reaction conditions in combination with (2) compounds containing chlorine bound anionically in the form of chloride suitable for activating said oxides and/or hydroxides under said reaction conditions forming chloride.

* * * * *